United States Patent
Swoyer et al.

(10) Patent No.: US 8,090,450 B2
(45) Date of Patent: Jan. 3, 2012

(54) PERCUTANEOUS ELECTRODE ARRAY AND SYSTEM

(75) Inventors: John M. Swoyer, Andover, MN (US); Jeff S. Gagnon, Champlin, MN (US); Richard M. Farrell, Grant, MN (US)

(73) Assignee: Greatbatch Ltd., Clarence, NY (US)

( * ) Notice: Subject to any disclaimer, the term of this patent is extended or adjusted under 35 U.S.C. 154(b) by 796 days.

(21) Appl. No.: 12/146,961

(22) Filed: Jun. 26, 2008

(65) Prior Publication Data
US 2009/0005844 A1 Jan. 1, 2009

Related U.S. Application Data

(60) Provisional application No. 60/946,701, filed on Jun. 27, 2007.

(51) Int. Cl.
*A61N 1/05* (2006.01)

(52) U.S. Cl. .............................. 607/117; 607/2; 607/116

(58) Field of Classification Search .................. 607/115, 607/117, 55, 136–137; 600/377–378
See application file for complete search history.

(56) References Cited

U.S. PATENT DOCUMENTS

| | | | |
|---|---|---|---|
| 4,630,611 A | 12/1986 | King | |
| 5,417,719 A | 5/1995 | Hull et al. | |
| 5,462,545 A | 10/1995 | Wang et al. | |
| 5,501,703 A | 3/1996 | Holsheimer et al. | |
| 5,643,330 A | 7/1997 | Holsheimer et al. | |
| 5,713,867 A | 2/1998 | Morris | |
| 6,064,905 A | 5/2000 | Webster, Jr. et al. | |
| 6,292,702 B1 | 9/2001 | King et al. | |
| 6,309,401 B1 | 10/2001 | Redko et al. | |
| 6,510,347 B2 | 1/2003 | Borkan | |
| 6,587,733 B1 | 7/2003 | Cross, Jr. et al. | |
| 6,745,079 B2 | 6/2004 | King | |
| 6,895,283 B2 | 5/2005 | Erickson et al. | |
| 7,146,224 B2 | 12/2006 | King | |
| 7,729,781 B2 * | 6/2010 | Swoyer et al. | ................ 607/116 |
| 2001/0023367 A1 | 9/2001 | King et al. | |

(Continued)

FOREIGN PATENT DOCUMENTS

DE 19758114 A1 12/1997

OTHER PUBLICATIONS

European Search Report, Nov. 11, 2008.

*Primary Examiner* — Carl H Layno
*Assistant Examiner* — Paula J Stice
(74) *Attorney, Agent, or Firm* — Michael F. Scalise

(57) ABSTRACT

Lead devices and methods for neurostimulation are described. Some of the neurostimulation leads provided have multiple, distal region electrode contacts arranged in an array capable of providing steerable spinal cord stimulation. In one use, a collapsed introducer sheath is disposed over a dilator and advanced to a spinal cord target site through a 14-gauge needle into the epidural space. The dilator is removed and the introducer is expanded to its full width. A neurological lead according to the present invention advanced through the introducer to near the target site and the introducer removed. The lead is wider than it is high and has a row of lower electrodes flanked by right and left side electrodes in groups of three. The lower electrodes serve as cathodes and the right and left electrodes are return anodes.

21 Claims, 5 Drawing Sheets

U.S. PATENT DOCUMENTS

| | | |
|---|---|---|
| 2002/0111661 A1 | 8/2002 | Cross et al. |
| 2002/0156513 A1 | 10/2002 | Borkan |
| 2004/0098074 A1 | 5/2004 | Erickson et al. |
| 2004/0127965 A1 | 7/2004 | Borkan |
| 2004/0186543 A1 | 9/2004 | King et al. |
| 2004/0186544 A1 | 9/2004 | King |
| 2005/0171587 A1 | 8/2005 | Daglow et al. |
| 2005/0203600 A1 | 9/2005 | Wallace et al. |
| 2005/0209667 A1 | 9/2005 | Erickson et al. |
| 2005/0256541 A1 | 11/2005 | Stypulkowski |
| 2005/0283216 A1 | 12/2005 | Pyles |
| 2006/0122678 A1 | 6/2006 | Olsen et al. |
| 2006/0206182 A1 | 9/2006 | Pyles |
| 2006/0253182 A1 | 11/2006 | King |
| 2006/0259110 A1 | 11/2006 | Wallace et al. |
| 2006/0271137 A1 | 11/2006 | Stanton-Hicks |
| 2007/0027514 A1 | 2/2007 | Gerber |
| 2007/0027515 A1 | 2/2007 | Gerber |
| 2007/0112403 A1* | 5/2007 | Moffitt et al. .......... 607/116 |
| 2007/0118198 A1 | 5/2007 | Prager |
| 2007/0135881 A1 | 6/2007 | Vilims |
| 2007/0150007 A1 | 6/2007 | Anderson et al. |
| 2007/0168008 A1 | 7/2007 | Olsen |
| 2007/0255372 A1 | 11/2007 | Metzler et al. |
| 2007/0255373 A1 | 11/2007 | Metzler et al. |
| 2008/0004675 A1 | 1/2008 | King et al. |

* cited by examiner

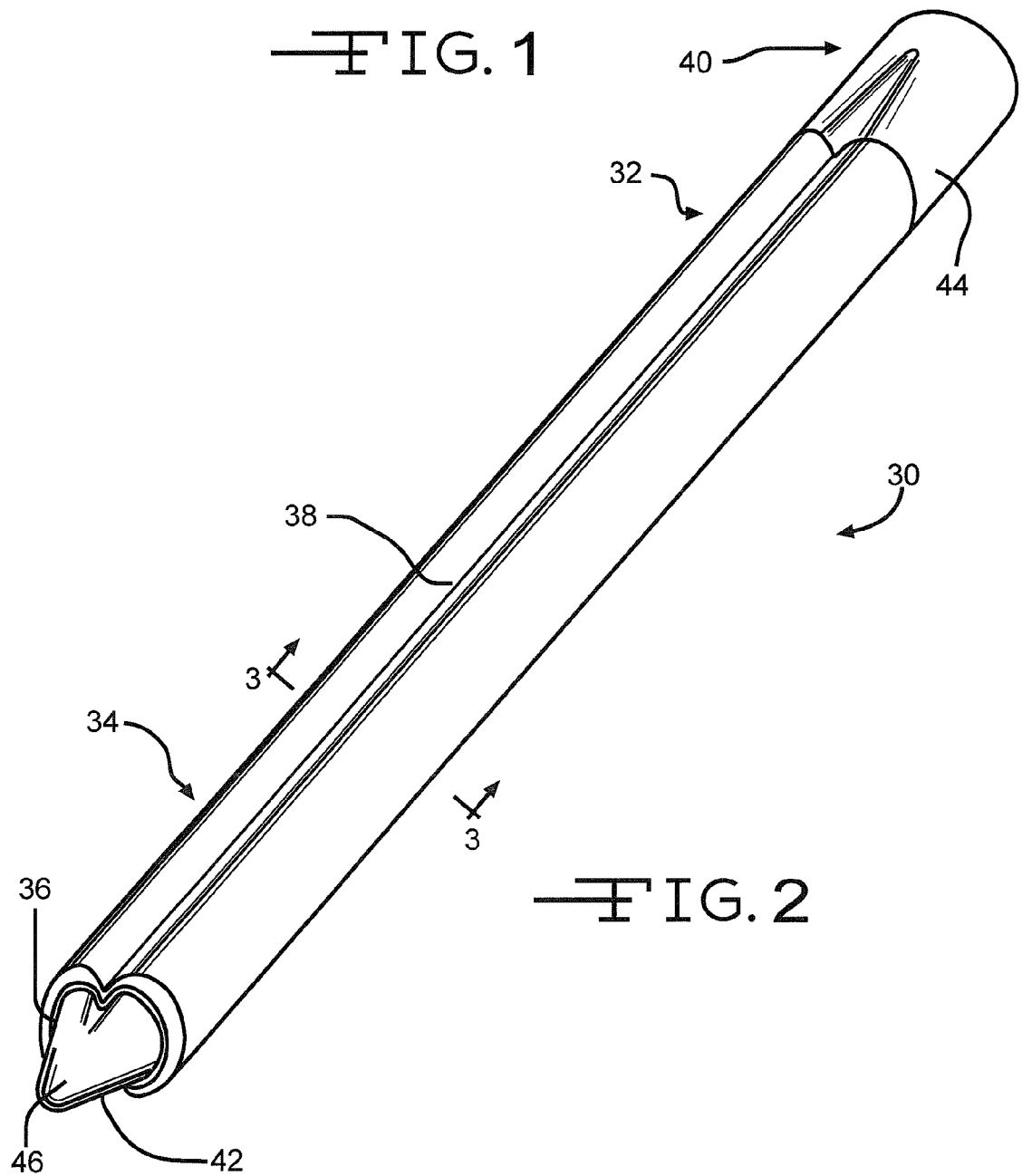

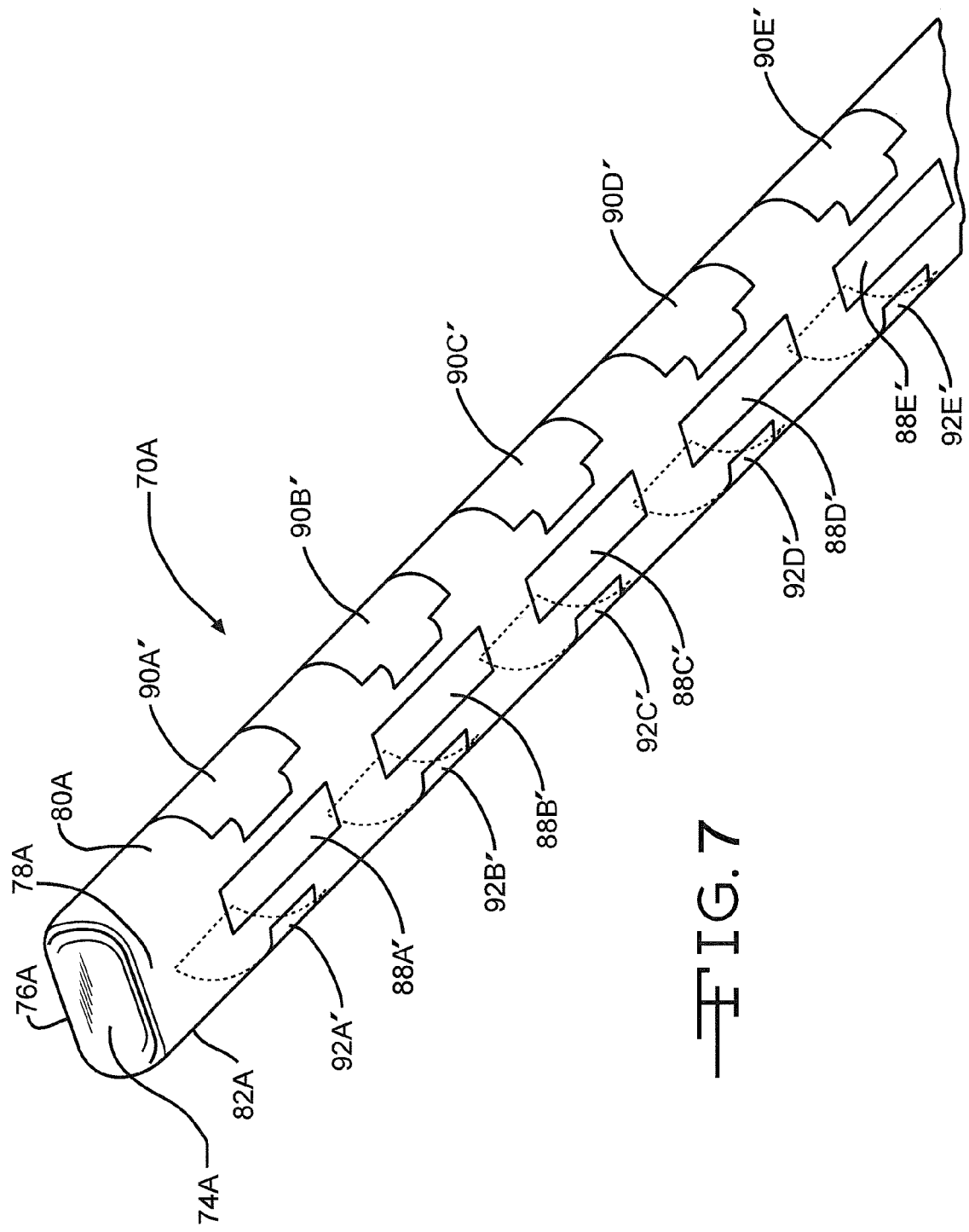

PERCUTANEOUS ELECTRODE ARRAY AND SYSTEM

CROSS-REFERENCE TO RELATED APPLICATION

The present application claims priority from U.S. Provisional Application Ser. No. 60/946,701, filed Jun. 27, 2007.

BACKGROUND OF THE INVENTION

1. Field of the Invention

The present invention is related generally to implantable medical electrical leads. More specifically, the present invention is related to implantable neurological leads.

2. Prior Art

Spinal cord and other neurological stimulations by electrical leads are used for many purposes, including pain masking. One lead design that has been particularly useful is the so called "transverse tripole" electrode arrangement. This contact arrangement includes a set of three electrodes positioned transversely to the axis of the spinal cord. The center electrode is generally the cathode, with either or both of the lateral electrodes acting as return anodes. It is desirable to have multiple sets of contacts to allow for reprogramming of the system to accommodate patient movement, change in disease state, and the like. The multiple sets of contacts may also be used to "steer" electrical stimulation into a desirable pattern.

For a transverse tripole contact arrangement, the current state of the art requires the percutaneous implantation of three separate electrode carrying leads. Each lead must be individually moved through an appropriately sized needle and properly positioned. Since positioning three leads requires multiple punctures with a needle, the procedure is understandably both challenging and time consuming. Alternatively, a surgical paddle type lead can be used. This requires an open surgical technique such as a laminotomy or laminectomy to place the paddle along the spinal cord. Needless to say, such invasive procedures are not desirable.

In that respect, a lead is needed that provides for percutaneous implantation of a multiple transverse tripole electrode array via a single standard needle stick. The presently described invention provides a lead with just such an electrode array.

SUMMARY OF THE INVENTION

The present invention is broadly directed to an implantable medical electrical lead, the lead comprising: an elongate body having a length extending from a proximal region to a distal region, wherein in cross-section transverse to its length, the lead body comprises an upper side, a lower side, a right side, and a left side; at least one first, center electrode supported by the lower side at the distal region of the lead body; at least one second, right electrode supported by the right side at the distal region of the lead body; and at least one third, left electrode supported by the left side at the distal region of the lead body.

The present invention is also directed to a method for electrically stimulating a target body site, comprising the steps of: providing a lead comprising: an elongate body having a length extending from a proximal region to a distal region, wherein in cross-section transverse to its length, the lead body comprises an upper side, a lower side, a right side, and a left side; at least one first, center electrode supported by the lower side at the distal region of the lead body; at least one second, right electrode supported by the right side at the distal region of the lead body; and at least one third, left electrode supported by the left side at the distal region of the lead body; advancing an introducer through a needle lumen to the body site, the introducer having a lumen housing a dilator therein; retracting the dilator from the introducer; advancing the electrical lead through the introducer; retracting the introducer and leaving the lead in place adjacent to the target body site with the at least one first, center electrode facing a body portion to be electrically stimulated and flanked on its right and left sides by the at least one second and thirds electrodes; and delivering electrical energy from the first, center electrode into the target body site with the second and third electrode serving as returns for the electrical energy.

These and other aspects of the present invention will become more apparent to those skilled in the art by reference to the following description and the appended drawings.

BRIEF DESCRIPTION OF THE DRAWINGS

FIG. 1 is a fragmentary, bottom view of a lead 10 according to the present invention having a distal region 14 with four electrodes 26 and a proximal region 18 with four conductor rings 28.

FIG. 2 is a perspective view of a collapsed introducer 30 having a dilator 40 housed therein with the introducer being in a collapsed configuration having a constrained, small transverse profile.

FIG. 5 is a fragmentary perspective view of the expanded introducer 60 of FIG. 4 having a neurological lead 70 advanced there through.

FIG. 7 is a fragmentary, perspective view from the lower side 78A of another embodiment of a lead 70A according to the present invention.

DETAILED DESCRIPTION OF THE PREFERRED EMBODIMENTS

Figure 3:
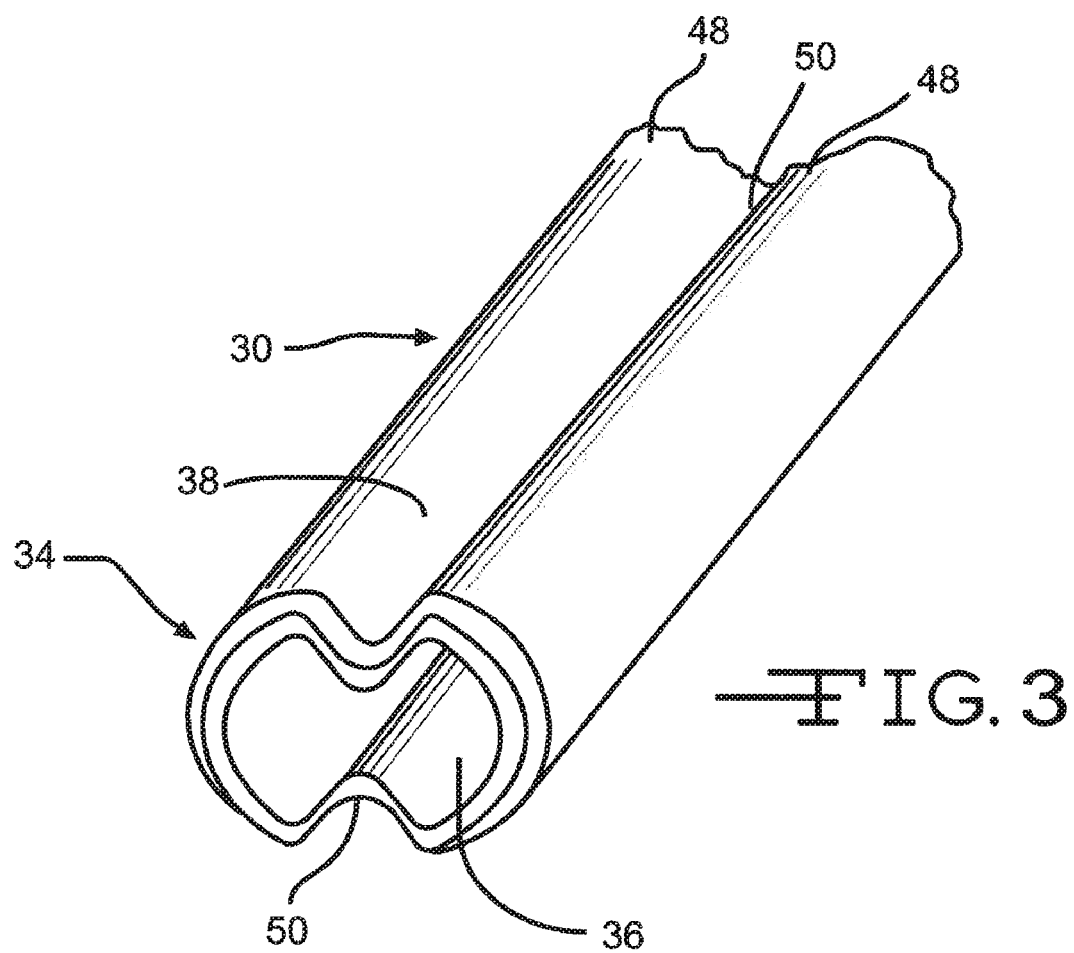
FIG. 3 is a cross-sectional view along line 3-3 of FIG. 2.

FIG. 1 is a generalized view of a neurological stimulation lead 10 according to the present invention. The lead 10 comprises a multi-conductor body 12 having a distal region 14 extending to a distal tip 16, a proximal region 18 extending to a proximal end 20 and an intermediate region 22 disposed between the distal and proximal regions. In one embodiment, the intermediate region 22 resides between the innermost distal and proximal electrical contacts described below. The lead body 12 can have an exterior surface or a tubular sidewall 24 formed of a polymeric material, for example, polyurethane or silicone.

The lead distal region 14 includes a number of electrodes (generally designated as 26 in FIG. 1) which may, for example, be cathodes disposed along the bottom of the lead body 12 in a spaced-apart configuration. The electrodes 26 may also be described as electrical contacts and are insertable into the human body for neurological stimulation. One exemplary use of electrodes 26 is the stimulation of the nerves within the spinal cord.

The proximal region 18 of the lead includes a number of connector bands or connector rings 28 disposed in a spaced-apart configuration and serving as electrical contacts or terminals. The distal electrodes 26 and the proximal connectors 28 are preferably formed of platinum, iridium, palladium, and combinations and alloys thereof. The connectors 28 can be used for connecting the lead 10 to a lead extension (not shown) for extending the effective length of the lead. In some uses, the connectors 28 directly couple the lead 10 to an implantable pulse generator (not shown).

The electrodes 26 and connectors 28 are preferably electrically coupled to each other in a one-to-one arrangement. In some leads, the distal-most electrode is electrically coupled to the distal-most connector, the second-to-distal-most electrode is electrically coupled to the second-to-distal-most connector, and so forth. The electrodes 26 and connectors 28 can be electrically coupled through conductors (not shown) extending between them. In some leads, the electrical conductors are embedded in the lead sidewall 24 while in others the electrical conductors lie within a lumen formed by the sidewall 24 extending the length of the lead. In some leads, the electrical conductors are disposed within a lumen that is provided with sufficient structural strength to withstand typical vascular forces without collapsing. This may include backfilling the lumen with a polymeric material, molding the lead sidewall 24 from a polymeric material with sufficient structural integrity or securing a strengthening member into the lumen, such as by gluing it in place. Some leads have stylet lumens for receiving a stiffening stylet member (not shown).

The lead 10 can be varied in outer diameter and length to suit a particular application for which it is intended. In some embodiments, the lead 10 has a total length of from about 5 cm to about 100 cm. In other embodiments, the lead 10 has an outer diameter of less than about 1 mm and a total length of from about 10 cm to about 150 cm.

FIGS. 2 and 3 illustrate an introducer sheath 30 having a proximal region 32, a distal region 34 including a distal port 36 leading to a lumen extending the entire length of the introducer, and a longitudinal region of preferential folding 38. The lumen within introducer 30 is clearly visible in FIG. 3. The introducer 30 is constrained in a first configuration having a relatively small transverse profile. This is accomplished by providing the introducer 30 with two longitudinal regions of preferential folding 38, preferably diametrically opposed to each other. Only the top such region is visible in the drawing. Other embodiments have more than two lines of preferential folding 38 to allow for increased inward folding of the introducer sidewall. The lines of preferential folding 38 can also be lines of preferential tearing or separation. Such lines of preferential tearing can be a weakened region that is scored part way through the thickness of the introducer sidewall.

The introducer 30 typically has a relatively thin sidewall that is not sufficiently strong to withstand being pushed into a vasculatory system, and the like, without collapsing. For that reason, a dilator 40 (FIG. 2) is disposed within the introducer lumen to provide internal stiffening. The dilator 40 has a length extending from a tapered distal tip 42 to a proximal region 44. The introducer 30 and dilator 40 are preferably cooperatively sized and configured with the introducer distal end or region 34 being releasably secured to the dilator 40 so that the introducer 30 is pulled through tissue or rides along with the dilator to the target site. That way, the tapered distal tip 42 facilitates moving the dilator 40 through the introducer 30 and for moving the introducer/dilator assembly through tissue or a vasculature.

In one embodiment, the introducer 30 and dilator 40 have an outer diameter sized sufficiently small to fit through a 12-gauge needle lumen. This is partially the result of the preferential folding regions 38 providing outwardly facing peaks 48 and inwardly facing valleys 50. The peaks 48 and valleys 50 extend along the majority of the length of the introducer 30 and dilator 40 and provide the assembly with a relatively low profile in cross-section. Other embodiments are sized to fit through a 14-gauge needle. A needle from 10- to 20-gauge may be used in various embodiments of the present dilator and introducer assembly.

For some applications, it may be useful to provide the dilator 40 with one or more distal mapping electrodes. That would be so that a user could determine that they are near or adjacent to an optimal stimulation location prior to deployment of the lead 10. One such electrode is shown at 46.

In some embodiments, a second dilator is advanced through the introducer 30 before a satisfactorily sized lumen is obtained. In other embodiments, the introducer is self expanding and does not require a second dilator to achieve a satisfactory configuration. Instead, the introducer material is sufficiently resilient and biased to open up when unconstrained. The introducer walls may also be formed of or include shape memory materials to urge the introducer to open when unconstrained. In still other embodiments, the introducer lumen is only partially opened when it is initially positioned in the body. However, the introducer material is pliable enough to permit an oversized lead to be advanced therethrough with the cross-sectional area of the lumen expanding as the lead passes.

Figure 4:
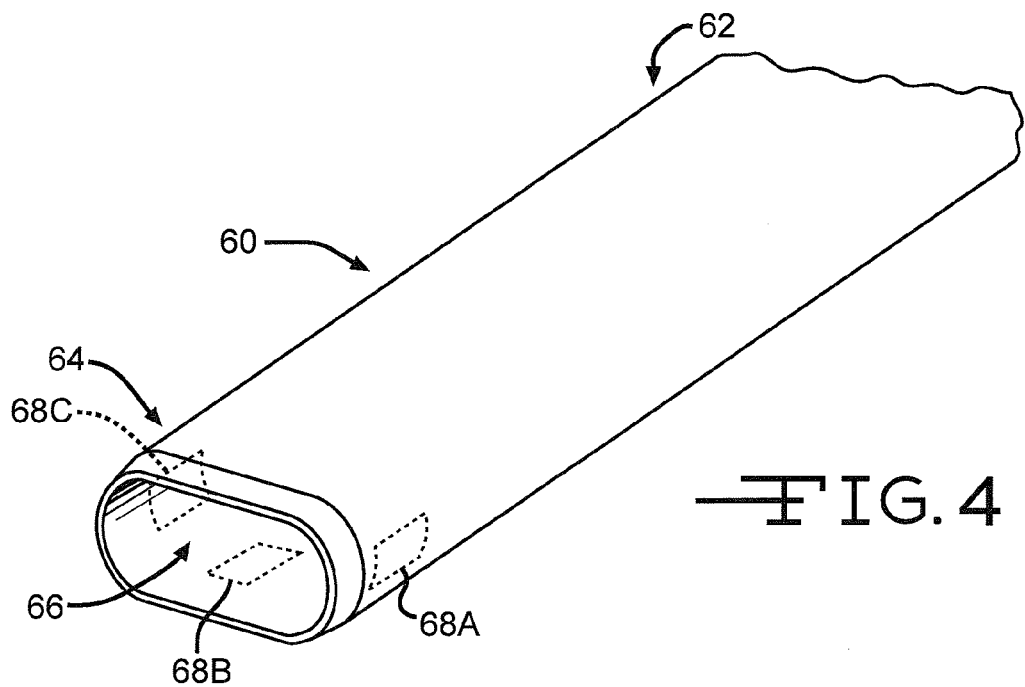
FIG. 4 is a fragmentary, perspective view of the introducer 30 shown in FIG. 2, but in an expanded shape after its transverse profile has been enlarged through self-expansion and/or expansion through dilation using a dilator and thereby given the numerical designation of an expanded introducer 60.

FIG. 4 illustrates the introducer 30 shown in FIGS. 2 and 3, but in an expanded configuration. For the sake of clarity, the expanded form of the introducer will be identified with numerical designation 60 while the collapsed or un-expanded form of the introducer will be identified with numerical designation 30.

The expanded introducer 60 has a proximal region 62 and a distal region 64 including a distal port 66 leading to a lumen extending the entire length of the introducer. The expanded introducer 60 has a relatively larger and wider oval-shaped profile in cross-section than when in its collapsed form shown in FIGS. 2 and 3. Distal electrodes 68A, 68B and 68C provide conductive outer regions useful for mapping. The introducer electrodes 68A, 68B and 68C are connected via electrical conductors (not shown) extending along the sidewall to connectors in the introducer proximal region 62.

Figure 5:
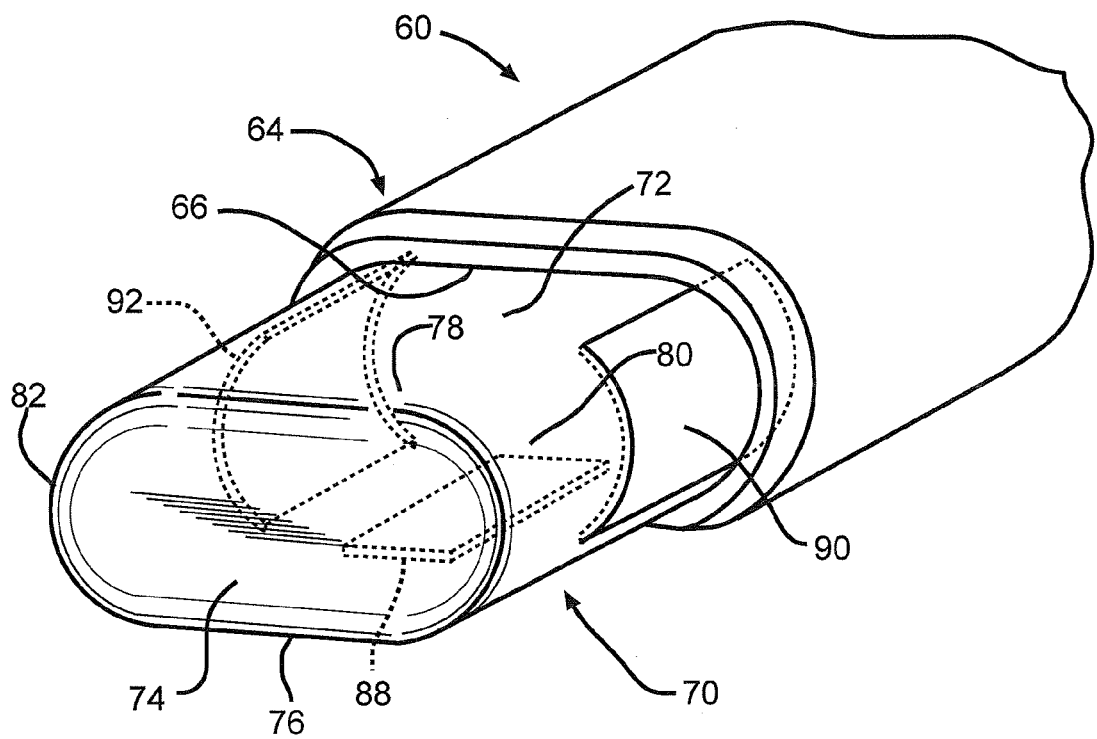
Figures 6, 6A:
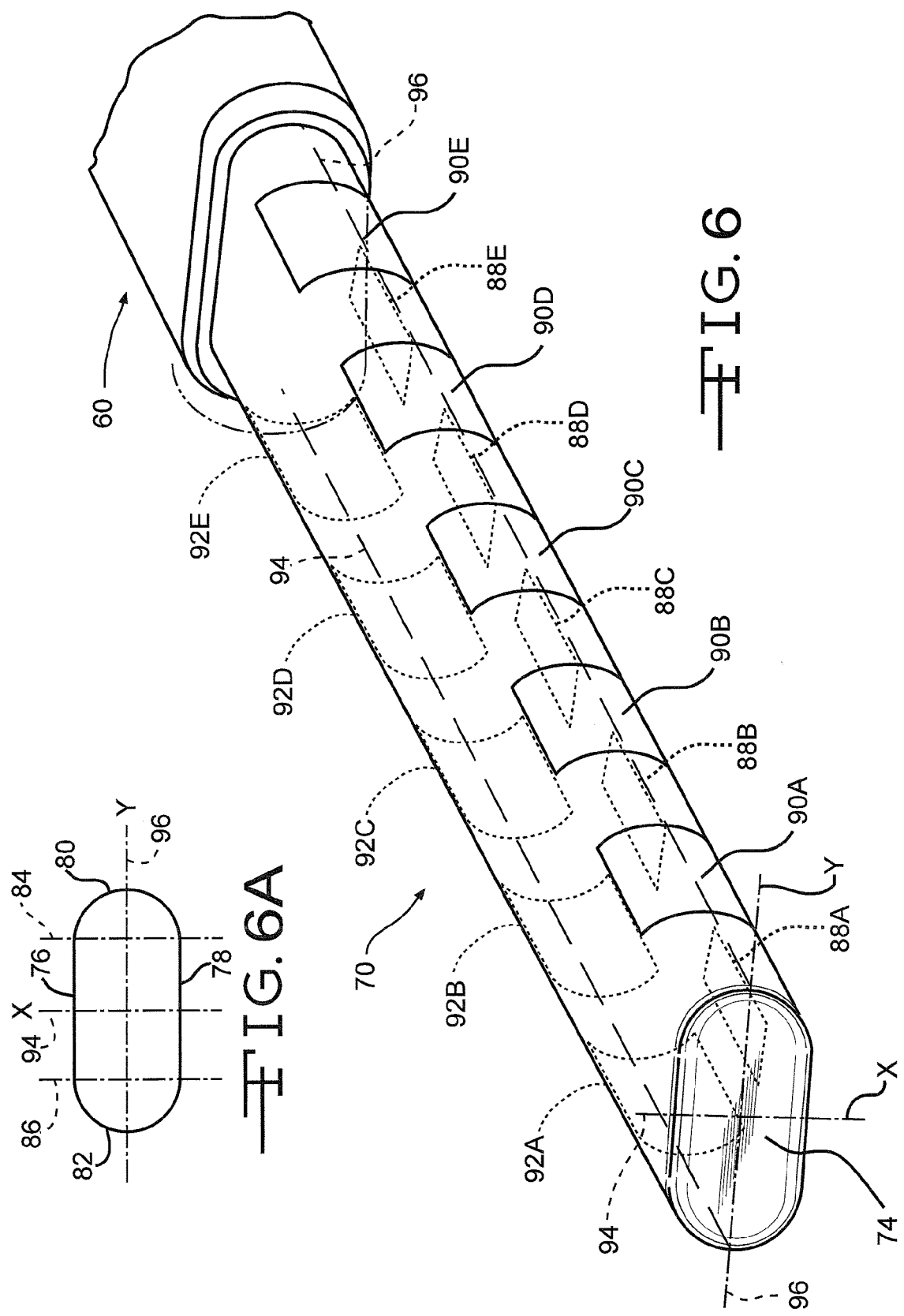
FIG. 6 is a perspective view of the expanded introducer 60 and lead 70 of FIG. 5 after the lead has been further advanced from the introducer or the introducer has been further retracted over the lead.
FIG. 6A is a cross-sectional schematic of the lead 70 shown in FIG. 6.

FIG. 5 illustrates the distal region 64 of the expanded introducer 60 with a neurological lead 70 according to the present invention being advanced from the distal port 66 thereof. The lead 70 comprises a sidewall 72 extending from a distal region 74 to a proximal end (not shown). The sidewall 72 provides the lead 70 with spaced apart upper and lower sides 76 and 78 extending to and meeting with right and left sides 80 and 82. The cross-sectional view shown in FIG. 6A illustrates that the upper and lower sides 76, 78 are generally planer while the right and left sides 80, 82 are radiused. Delineation between the upper side 76 and the right side 80 is indicated by the dashed line 84 as is delineation between the right side 80 and the lower side 78. Delineation between the lower side 78 and the left side 82 is indicated by the dashed line 86 as is delineation between the left side 82 and the upper side 76.

According to the present invention, the lead 70 has a tri-pole electrode configuration comprising at least one bottom electrode or contact 88A (shown in phantom) supported on or by the lower side 78 and serving as a cathode centered between at least one electrode or contact 90A supported on or by the right side 80 and at least one electrode or contact 92A (shown in phantom) supported on or by the left side 82. The right and left contacts 90A, 92A serve as anodes. There are no electrodes on the upper side 76 of the lead 70. The terms left side and right side are used interchangeably, as it is expected that in most embodiments the two sides will be identical to each other and symmetric, although in some embodiments that may not be the case.

FIG. 6 also shows that the electrodes 88A to 88E, 90A to 90E and 92A to 92E have a generally rectangular shape. However, that is not necessary. The electrode can be radiused in the form of circular contacts, or have both linear and radius portions in the shape of ovals. If fact, the electrode can have a myriad of different shapes only limited by the particular application for which the lead is designed.

While at least one center electrode 88A flanked by right and left electrodes 90A, 92A is the minimum number contemplated for a tri-pole electrical lead according to the present invention, most lead embodiments will have multiples of this electrode configuration. An example is shown in FIG. 6 where the lead 70 has five center electrodes 88A, 88B, 88C, 88D and 88E flanked on the right by electrodes 90A, 90B, 90C, 90D and 90E and on the left by electrodes 92A, 92B, 92C, 92D and 92E. A different number of combinations of center, right and left electrodes or contacts are possible. Some leads have two, three, four, five, six, seven, eight, or even more tri-pole electrode combinations. In any event, it is preferred that the respective electrodes do not extend past the lines 84, 86 delineating the bottom side 78 from the right and left sides 80, 92.

FIG. 6A also shows that the lead 70 is symmetric in cross-section along an x-axis indicated by the dashed line 94 and along a y-axis indicated by the dashed line 96. The x- and y-axes 94, 96 bisect the lead body 70. The bottom electrodes 88A to 88E are generally centered on the x-axis 94 while the right electrodes 90A to 90E and the left electrodes 92A to 92E are generally centered on the y-axis 96. In some embodiments, the center, right and left electrodes are not centered, but the majority of their exposed surface areas reside on the bottom, right or left sides, as the case may be. In still other embodiments, the right and left side electrodes 90A to 90E and 92A to 92E extend slightly under the lead body onto the lower side 78. An example of this is shown in FIG. 7 at the distal region 74A of lead 70A where electrodes 90A', 90B', 90C', 90D' and 90E' reside on the right side 80A of the lead and electrodes 92A', 92B', 92C', 92D' and 92E' reside on the left side 78A of the lead, but have a portion of their surface areas extending onto the lower side 78A opposite the upper side 76A. In other embodiments, the side electrodes 90A' to 90E', 92A' to 92E' may extend around to the upper side 76A of the lead body 70.

As some modern stimulation generators have a total of 16 electrical contacts, a lead according to the present invention could have 16 channels. In the present invention, providing the electrodes in groups that are divisibility by three is not necessary. For example, there could be a center column of eight electrodes flanked by right and left columns of eight electrodes or a center column of six electrodes flanked by right and left columns of five electrodes. The spacing of the outer right and left electrode arrays could be staggered with respect to the center columnar electrode array. Other exemplary embodiments could include splitting a total of 24 electrodes into three columns of eight or have a configuration of ten center electrodes flanked by seven on either side.

The lead 70 has a body formed of a polymeric material well known to those skilled in the art. The electrodes 88A to 88E, 90A to 90E and 92A to 92E are formed of suitably conductive materials, for example platinum, iridium, palladium, and combinations and alloys thereof. Some leads have each electrode individually addressable, while others have the respective side electrodes 90A to 90E, 92A to 92E electrically connected to each other.

In use, a 14-gauge needle, or a range of sizes from 10 to 20-gauge, is used to access the epidural space using access methods similar to those currently in use. The collapsed introducer 30 and corresponding dilator 40 are passed through the needle into the epidural space and positioned near the stimulation target. The "collapsed" dilator is then removed, allowing the introducer to assume its expanded form. It may be necessary to manually expand the introducer with an expanding dilator. Alternatively, just passing the lead 70 may expand the introducer. The lead 70 is then moved through and out of the expanded introducer 60 so that the at least one central cathode electrode 88A faces towards the spinal cord flanked on either side by the at least one right and left electrodes 90A and 92A. The electrode may be stylet driven and positioned much like current percutaneous electrodes.

Some features of the electrode design include a directional set of one or more cathodes. The cathodes can be facing the spinal cord, limiting the amount of current flowing into "non-target" tissue. This improves electrical efficiency and limits potential adverse effects of stimulating tissue such as muscle, etc. The edge or side contacts 90A, 92A are not directional and typically act as the anode, or electrical return path. As such, stimulation is not anticipated at the anodes. In other embodiments, the side contacts 90A, 92A act as cathode and the center electrode 88A is the return anode. In any event, close contact spacing between the cathodes and anodes is desirable for many embodiments. That way, the electrical field can be "steered" to the stimulation target by careful design of the spacing and electrical properties of the at least one cathode and the at least one anode.

Another benefit of the present invention is that the lead 70 has an aspect ratio that is wider along the y-axis than it is high along the x-axis in many embodiments. The width is a factor of from about 1.5 times to about 10× the height, preferably from about 3× to about 5× the height of the lead 70. This helps stabilize the lead 70 and electrodes into the appropriate orientation by making it difficult to "flip" the lead once it is positioned. In many embodiments, the lead body along much of its length is essentially the same dimensionally as the lead distal region 74 carrying the electrodes. This limits the opportunity for tissue in-growth around the lead 70, thereby allowing for easier lead repositioning or removal. In some embodiments, the proximal region of the lead 70 is split into multiple sets of connector contacts for compatibility with a pulse generator.

Some embodiments of the lead 70 have a steerable distal tip, for example, controllably deflectable from the introducer's 30/60 proximal region. Some introducers 30/60 have one or more electrode contacts at the introducer distal tip. Some introducers may be slittable or splittable, to allow for removing the introducer from over the lead 70 without having to slide the introducer over the lead's proximal end. Such introducers may have a region of preferential weakness, such as a scored or perforated region. A proximal slitter may be used in some embodiments to slit the introducer as it is being removed from the lead. In some embodiments, the dilator has one or more distal region electrodes which may be used for mapping or other purposes, both prior to and after the lead 70 has been positioned.

It is appreciated that various modifications to the inventive concepts described herein may be apparent to those of ordinary skill in the art without departing from the spirit and scope of the present invention as defined by the appended claims.

What is claimed is:

1. An implantable medical electrical lead, the lead comprising:
    a) an elongate body having a length extending from a proximal region to a distal region, wherein in cross-section, transverses to its length, the distal region of the lead body comprises a planar upper side, a planar lower side, a radiused right side, and a radiused left side with the radiused right and left sides extending to and meeting with the planar upper and lower sides to provide the distal lead region with an oval-shape in cross-section;
    b) at least one first, center electrode supported by the lower side at the distal region of the lead. body;
    c) at least one second, right electrode supported by the right side at the distal region of the lead body; and
    d) at least one third, left electrode supported by the left side at the distal region of the lead body,
    e) wherein the second and third electrodes are of an opposite polarity in comparison to the first electrode, and
    f) wherein a portion of at least one of the second, and third electrodes extends onto the lower side of the lead adjacent to the opposite polarity first electrode, and
    g) wherein the at least one first, second and third electrodes are aligned with each other along a transverse axis, perpendicular to a longitudinal axis of the lead body.

2. The lead of claim 1 wherein there are a plurality of the first, second and third electrodes in groups of three.

3. The lead of claim 1 wherein there are more center electrodes than right and left electrodes.

4. The lead of claim I wherein there are fewer center electrodes than right and left electrodes.

5. The lead of claim 1 wherein the at least one of the first, second and third electrodes are individually, electrically addressable through conductors extending to the lead body proximal region.

6. The lead of claim 1 wherein the second, right side electrode and the third, left side electrode extend to the planar upper side of the lead.

7. The lead of claim 1 wherein the lead body distal region has an aspect ratio of width to height of from about 1.5 to 10.

8. The lead of claim I wherein the at least one first, second and third electrodes are centered along the respective lower, right and left sides of the lead body.

9. The lead of claim 1 wherein the at least one first electrode is a cathode and the at least one second and third electrodes are return anodes.

10. The lead of claim 1 wherein the at least one first electrode is an anode and the at least one second and third electrodes are cathodes.

11. An implantable medical electrical lead, the lead comprising:
    a) an elongate body having a length extending from a proximal region to a distal region, wherein in cross-section, transverses to its length, the distal region of the lead body comprises a planar upper side, a planar lower side, a radiused right side, and a radiused left side with the radiused right and left sides extending to and meeting with the planar upper and lower sides to provide the distal lead region with an oval-shape in cross-section;
    b) a plurality of first, center electrode supported by the lower side at the distal region of the lead body;
    c) a plurality of second, right electrode supported by the right side at the distal region of the lead body;
    d) a plurality of third, left electrode supported by the left side at the distal region of the lead body; and
    e) wherein the first, second and third electrodes are aligned with each other in groups of three along a transverse axis, perpendicular to a longitudinal axis of the lead body,
    f) wherein the second and third electrodes are of an opposite polarity in comparison to the first electrode, and
    g) wherein a portion of both of the second and third electrodes extends onto the lower side of the lead adjacent to the opposite polarity first electrode, and
    h) wherein the at least one first, second and third electrodes are aligned with each other along a transverse axis, perpendicular to a longitudinal axis of the lead body.

12. An implantable medical electrical lead, the lead comprising:
    a) an elongate body having a length extending from a proximal region to a distal region, wherein in cross-section, transverses to its length, the distal region of the lead body comprises a planar upper side, a planar lower side, a radiused right side, and a radiused left side with the radiused right and left sides extending to and meeting with the planar upper and lower sides to provide the distal lead region with an oval-shape in cross-section;
    b) at least one first, center electrode supported by the lower side at the distal region of the lead body;
    c) at least one second, right electrode supported by the right side at the distal region of the lead body; and
    d) at least one third, left electrode supported by the left side at the distal region of the lead body,
    e) wherein the second and third electrode are of an opposite polarity in comparison to the first electrode, and
    f) wherein a portion of both of the second and third electrodes extends onto the lower side of the lead adjacent to the opposite polarity first electrode, and
    g) wherein the at least one first, second and third electrodes are aligned with each other along a transverse axis, perpendicular to a longitudinal axis of the lead body.

13. The lead of claim 12 wherein there are a plurality of the first, second and third electrodes in groups of three.

14. The lead of claim 12 wherein there are more center electrodes than right and left electrodes.

15. The lead of claim 12 wherein there are fewer center electrodes than right and left electrodes.

16. The lead of claim 12 wherein the at least one of the first, second and third electrodes are individually, electrically addressable through conductors extending to the lead body proximal region.

17. The lead of claim 12 wherein the second, right side electrode and the third, left side electrode extend to the planar upper side of the lead.

18. The lead of claim 12 wherein the lead body distal region has an aspect ratio of width to height of from about 1.5 to 10.

19. The lead of claim 12 wherein the at least one first, second and third electrodes are centered along the respective lower, right and left sides of the lead body.

20. The lead of claim 12 wherein the at least one first electrode is a cathode and the at least one second and third electrodes are return anodes.

21. The lead of claim 12 wherein the at least one first electrode is an anode and the at least one second and third electrodes are cathodes.

* * * * *